United States Patent [19]

Torget et al.

[11] Patent Number: 5,705,369
[45] Date of Patent: Jan. 6, 1998

[54] PREHYDROLYSIS OF LIGNOCELLULOSE

[75] Inventors: Robert W. Torget, Littleton; Kiran L. Kadam; Teh-An Hsu, both of Golden; George P. Philippidis, Highlands Ranch; Charles E. Wyman, Lakewood, all of Colo.

[73] Assignee: Midwest Research Institute, Kansas City, Mo.

[21] Appl. No.: 443,693

[22] Filed: May 18, 1995

Related U.S. Application Data

[63] Continuation of Ser. No. 364,560, Dec. 27, 1994, Pat. No. 5,503,996.
[51] Int. Cl.⁶ .......................... C12P 19/02; C12P 19/14; C12N 9/26
[52] U.S. Cl. .......................... 435/105; 127/1; 127/37; 435/99; 435/101; 435/136; 435/148; 435/157; 435/163; 435/201; 536/111; 536/56; 536/57; 536/124
[58] Field of Search .................. 435/101, 99, 105, 435/136, 148, 157, 163, 201; 536/1.11, 57, 124, 56; 127/1, 37

[56] References Cited

U.S. PATENT DOCUMENTS 5,424,417  6/1995  Torget et al. .................. 127/1

Primary Examiner—Herbert J. Lilling
Attorney, Agent, or Firm—Edna M. O'Connor; Ken Richardson; Ruth Eure

[57] ABSTRACT

The invention relates to the prehydrolysis of lignocellulose by passing an acidic or alkaline solution through solid lignocellulosic particles with removal of soluble components as they are formed. The technique permits a less severe combination of pH, temperature and time than conventional prehydrolysis. Furthermore, greater extraction of both hemicellulose and lignin occurs simultaneously in the same reactor and under the same conditions.

14 Claims, 7 Drawing Sheets

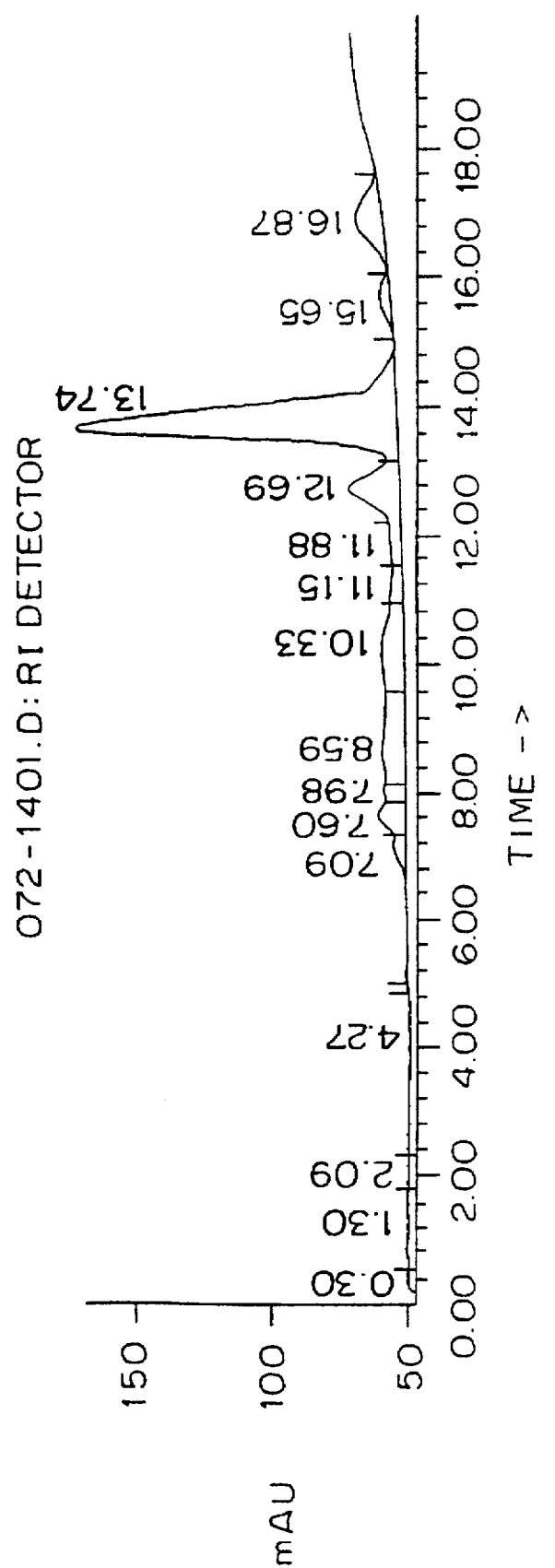

PREHYDROLYSIS OF LIGNOCELLULOSE

This is a Continuation of application Ser. No. 08/364,560 filed Dec. 27, 1994 now U.S. Pat. No. 5,503,996.

The United States Government has rights in this invention under Contract No. DE ACO2-83CH10093 between the United States Department of Energy and the National Renewable Energy Laboratory, a division of the Midwest Research Institute.

FIELD OF THE INVENTION

The invention relates to certain improvements in the prehydrolysis of lignocellulosic feedstocks to fractionate it into hemicellulose, cellulose and lignin. The carbohydrate fractions may then be hydrolysed into sugars and fermented to produce alcohol and other products.

BACKGROUND TO THE INVENTION

Lignocellulose is ubiquitous in all wood species and all agricultural and forestry waste. In addition, municipal waste which typically contains about half waste paper and yard waste, is a source of lignocellulosic materials. Currently, municipal waste is buried or burned at considerable expense to the disposer or the government organization providing solid waste services.

Lignocellulosic biomass is a complex structure of cellulose fibers wrapped in a lignin and hemicellulose sheath. The ratio of the three components varies depending on the type of biomass. Typical ratios are as follows:

|  | Softwoods | Corn cobs | RDF* |
| --- | --- | --- | --- |
| Cellulose | 42% | 40% | 52% |
| Hemicellulose | 25% | 36% | 26% |
| Lignin | 28% | 13% | 20% |

*RDF = Refuse Derived Fuel from municipal systems waste

Different woods also have different compositions. Softwoods (gymnosperms) generally have more glucommanans and less glucuronoxylans than hardwoods and grasses (angiosperms).

Cellulose is a polymer of D-glucose with $\beta[1\rightarrow 4]$ linkages between each of the about 500 to 10,000 glucose units. Hemicellulose is a polymer of sugars, primarily D-xylose with other pentoses and some hexoses with $\beta[1\rightarrow 4]$ linkages. Lignin is a complex random polyphenolic polymer. Therefore, lignocellulose represents a very cheap and readily available substrate for the preparation of sugars which may be used alone or microbially fermented to produce alcohols and other industrial chemicals.

Ethanol, one of the alcohols which can be produced from lignocellulosic biomass, has a number of industrial and fuel uses. Of particular interest is the use of ethanol as an additive to gasoline to boost octane, reduce pollution and to partially replace gasoline in the mixture. This composition is the well known commercial product called "gasohol". It has been proposed to eliminate gasoline completely from the fuel and to burn ethanol alone. Such a fuel would produce considerably less air pollution by not forming as much carbon monoxide or hydrocarbon emissions. Furthermore, gasoline is produced from crude oil which fluctuates in price, availability and is the subject of unpredictable world politics.

It has been estimated that about $1\times 10^9$ tons of lignocellulosic wastes are produced every year. This amount exceeds the total amount of crude oil consumed per year. In theory, if properly managed, the lignocellulose produced by the United States is sufficient to produce all of the country's needs for liquid fuel if the cellulose and hemicellulose can be completely converted into ethanol. The amount of energy theoretically obtainable from the combustion of cellulose or the glucose or alcohol derived therefrom is about 7200 BTU per pound or roughly equivalent to 0.35 pounds of gasoline. Hemicellulose has similar value when converted into sugars or ethanol. Consequently, cellulose and hemicellulose represents a readily available potential source for ethanol production.

The technology for the production of ethanol from grain and fruit for beverage purposes has been well developed for centuries. However, the costs have been relatively high compared to the cost of gasoline. Accordingly, many methods have been proposed to reduce the cost and increase the efficiency of ethanol production.

Among the techniques proposed for the production of fuel grade ethanol include the hydrolysis of cellulose to produce glucose which can be fermented to produce ethanol. Cellulose in the form of wood, newsprint and other paper, forest, agricultural, industrial and municipal wastes is quite inexpensive compared to grain, fruit, potatoes or sugarcane which is traditionally used to prepare alcohol beverages.

Cellulose hydrolysis using an acid catalyst to produce sugars has been known for decades but can be costly and requires special equipment. The sugars themselves, are somewhat labile to the harsh hydrolysis conditions and a large number of unwanted or toxic byproducts may be formed. If exposed to acid for too long, the glucose derived from cellulose degrades into hydroxymethylfurfural which can be further degraded into levulinic acid and formic acid. Xylose, which is formed from hemicellulose, is degraded by acids into furfural and then results in tars and other degradation products.

In order for acid to completely hydrolyse the cellulose and hemicellulose in a lignocellulosic substrate, degradation of the desirable sugars and formation of the toxic byproducts cannot be avoided due to kinetic constraints. To use conditions sufficiently gentle that insignificant degradation of sugars will occur does not result in complete hydrolysis of substrate. Furthermore, the acid is corrosive and requires special handling and equipment. Accordingly, in the last twenty years attention has focused on enzymatic hydrolysis of cellulose with cellulase followed by fermentation of the resulting sugars to produce ethanol which in turn is distilled to purify it sufficiently for fuel uses.

Cellulase is an enzyme complex that includes three different types of enzymes involved in the saccharification of cellulose. The cellulase enzyme complex produced by Trichoderma reesei QM 9414 contains the enzymes named endoglucanase (E.C.3.2.1.4), cellobiohydrolase (E.C.3.2.1.91) and $\beta$-glucosidase (E.C.3.2.1.21). Gum et al, *Biochem. Biophys. Acta*, 446:370–86 (1976). The combined synergistic actions of these three enzymes in the cellulase preparation completely hydrolyses cellulose to D-glucose.

However, cellulase can not completely degrade the cellulose found in native, unpretreated lignocellulose. It appears that the hemicellulose and lignin interfere with the access of the enzyme complex to the cellulose, probably due to their coating of the cellulose fibers. Furthermore, lignin itself can bind cellulase thereby rendering it inactive or less effective for digesting cellulose. For example, raw ground hardwood is only about 10 to 20% digestible into sugars using a cellulase preparation.

To overcome these shortcomings, applicants and others have previously disclosed a pretreatment step which attempts to degrade or remove at least a portion of the hemicellulose and/or lignin. The result of the pretreatment has been greater digestibility of the cellulose by a cellulase complex. One such pretreatment has been the use of a comminution step and a combination of heat and acid for a period of time which hydrolyses most of the hemicellulose, thus rendering the cellulose digestible by a cellulase complex.

In the prior art, by using such a pretreatment step, little lignin has been removed. See Grohmann et al, Biotechnology and Bioengineering, Symp. No. 17:135-151 (1986), Torget et al, Applied Biochemistry and Biotechnology, 24/25:115-126 (1990), Torget et al, Applied Biochemistry and Biotechnology, 28/29:75-86 (1991) and Torget et al, Applied Biochemistry and Biotechnology, 34/35:115-123 (1992).

Lignin removal from cellulosic fibers by a caustic (alkali) is the basis for Kraft pulping and paper making. However, such techniques are aimed at conserving the polymeric carbohydrate integrity and thus do not produce simple sugars, and do not separate the hemicellulose from the cellulose.

The difficulty of degrading the hemicellulose and cellulose remains. Conditions optimized to remove hemicellulose are not very effective at removing lignin and vice versa. Therefore, the cellulose remaining after prehydrolysis may be less than ideally separated from the other constituents and may retard digestion by cellulase. Furthermore, the costs involved for the pretreatment step can be significant. The chemicals used to alter pH and the steam required to heat the lignocellulose add a cost to the process. The greater the duration of the prehydrolysis step, the greater cost in heat to maintain the temperature; and the slower the overall process, also the greater cost in time and equipment.

Elian et al, U.S. Pat. No. 2,734,836, discloses a process where acid is used to pretreat cellulosic materials to extract pentoses using acetic acid. The material is sprinkled with the acid and heated to 80°-120° C. and the acid is recycled through the cooker in a manner to preserve the cellulose fibers. The residual material is used in conventional pulping.

Richter, U.S. Pat. No. 3,532,594, discloses digesting cellulosic material by soaking the solids in an alkaline liquid, and then applying steam in a gas phase to heat the material. The material is cooled and washed to recover cellulosic fibers. The digestion of the non-cellulose occurs in the gas phase as wood chips descend in the reactor. No reaction is occurring in the countercurrent washing step.

Eickemeyer, U.S. Pat. No. 3,787,241, discloses a percolator vessel for decomposing portions of wood. The first stage is the hydrolysis of hemicellulose to xylose using 1% sulfuric acid (column 4, lines 23-34) and then acid hydrolysis of cellulose occurs later. Lignin remains in the reactor throughout the hydrolysis and is removed at the end.

Pfeiffer, U.S. Pat. No. 4,226,638, discloses an acid pretreatment of young plants where the acid is not permitted to saturate the young plants. Column 3, line 59 specifically states that the amount of saturation is less than 70% and line 67 states that 60% of the xylan is hydrolysed. The wash step is performed by water. The goal is to extract xylose form plant material.

Brink, U.S. Pat. No. 4,384,897 and later 5,221,357, uses a nitric acid two stage hydrolysis where the first stage is under mild conditions to hydrolyse the hemicellulose. (pH 2-3, 140°-220° C.) Later harsher acidic conditions are used to hydrolyse the cellulose present which is then washed free from the lignin. No lignin is removed during the hydrolysis. The liquid and biomass particles travel in a cocurrent flow pattern according to column 10 lines 1-5 of the more recent patent.

Elmore, U.S. Pat. No. 4,436,586, describes a method for treating wood chips by acid prehydrolysis to extract xylose for fermentation to ethanol and preserves the cellulose fibers and lignin for kraft pulping of the residual solids. The pretreatment is in a reactor with filtering screens and recycling of the acid.

Tourier et al, U.S. Pat. No. 4,511,433, describes a continuous extraction process where wood is placed in a reactor 1 and is retained by filter 2 where a strongly acidic solution is passed through the system to remove pentoses. The acidic solution is mixed with a phenol compound in a different phase to remove lignin. The two phase system is needed for Tourier to achieve their results.

Neves, U.S. Pat. No. 4,564,595, discloses a process which includes cellulose cooking and degradation with acid. The process separates hemicellulose from the pretreated material and in a separate step removes lignin. According to the second paragraph in column 7, agitation of the mixture appears essential to adequate extraction.

Sherman et al, U.S. Pat. No. 4,612,286 and later U.S. Pat. No. 4,668,340, hydrolyse the hemicellulose in a high solids system by a complex process of passing a 20-40% solids slurry of biomass into the bottom of a reactor and passing acid through a series of screens and solid-liquid separators to wash the hydrolysed C5 sugars in a separate location which are then withdrawn as hydrolyzate. According to column 2, line 37, the acid concentration in the reaction chamber is about 2% to 10%. Conditions are chosen so that cellulose is not hydrolysed. The remaining solids include cellulose and lignin which are burned or if separated, must be done in a separate step.

Wright, U.S. Pat. No. 4,615,742, discloses a series of hydrolysis reactors. Some of these are prehydrolysis reactors and are for removing hemicellulose while others are for hydrolysis. Because the contents move in a series, the duration of each step is the same. The process does not remove lignin from the solids and multiple reactors are required. Within each reactor is a predefined set of conditions.

Rehberg, U.S. Pat. No. 4,995,943, pretreats biomass with high pressure carbon dioxide and then suddenly releases it to open up the material to allow better degradation of cellulose. The gas applied is described as anhydrous and therefore should not contain carbonic acid other than that which forms in situ. The purpose of the Rehberg process is unrelated to any prehydrolysis process as water is not present in appreciable amounts.

Grohmann et al, U.S. Pat. No. 5,125,977, demonstrated that different xylans could be removed during prehydrolysis under two different conditions by prehydrolyzing the substrate, centrifuging the mixture to recover xylose from certain xylans in the supernatant. The solids were remixed with additional acid, the prehydrolysis completed and a second xylose solution produced by apparently different xylans in the hemicellulose. The two types of xylan are hydrolysed by two different conditions which are optimized for each xylan.

SUMMARY OF THE INVENTION

It is an object of the present invention to overcome the previous difficulties in prehydrolyzing lignocellulosic material.

It is another object of the present invention to use a less severe combination of conditions to effect prehydrolysis of lignocellulose.

It is a further object of the present invention to separate a greater percentage of hemicellulose and lignin from cellulose in a lignocellulosic substrate.

It is yet another object of the present invention to prepare a cellulosic material which is more easily digested by a given amount of cellulase and a hydrolyzate liquid with a greater proportion of the hemicellulose and lignin.

It is still another object of the present invention to enzymatically produce sugars from pretreated lignocellulosic substrates.

It is still a further object of the present invention to produce a liquid and solid stream containing carbohydrates from a lignocellulosic feedstock which are amenable to fermentation processes to produce alcohol and other industrial chemicals.

It is an additional object of the present invention to separate liquid products produced by prehydrolysis from a solid residue during the prehydrolysis before the conditions are returned to ambient conditions.

It is yet another object of the present invention to vary the conditions of time, temperature and acid concentration in a single reactor during a single prehydrolysis step by using the concept of a varying combined severity factor so that the resultant solid residue is amenable to enzymatic saccharification as well as acid catalyzed saccharification.

It is yet an additional object of the present invention to adjust the pH before enzymatic saccharification of cellulose in such a way that the product of neutralization, i.e. gypsum, is less soluble and thus removed to a greater extent.

The present invention utilizes a flow-through reactor such as a percolation reactor containing lignocellulosic substrate where prehydrolysis fluid is passed through the lignocellulosic substrate and removed while still hot. The fluid may be further treated to completely hydrolyze any sugar polymers or oligomers. The solid residue from the prehydrolysis reactor, after being washed with reaction temperature water in the reactor, is then contacted with cellulase to saccharify the cellulose into sugars. Both sugar solutions may be fermented separately, together and/or simultaneously to produce industrial chemicals such as ethanol with the cellulase saccharifying the cellulose.

BRIEF DESCRIPTION OF THE DRAWINGS

FIG. 3a is the result of HPLC separation of components of the prehydrolyzate.

DESCRIPTION OF THE PREFERRED EMBODIMENT

Figure 1:
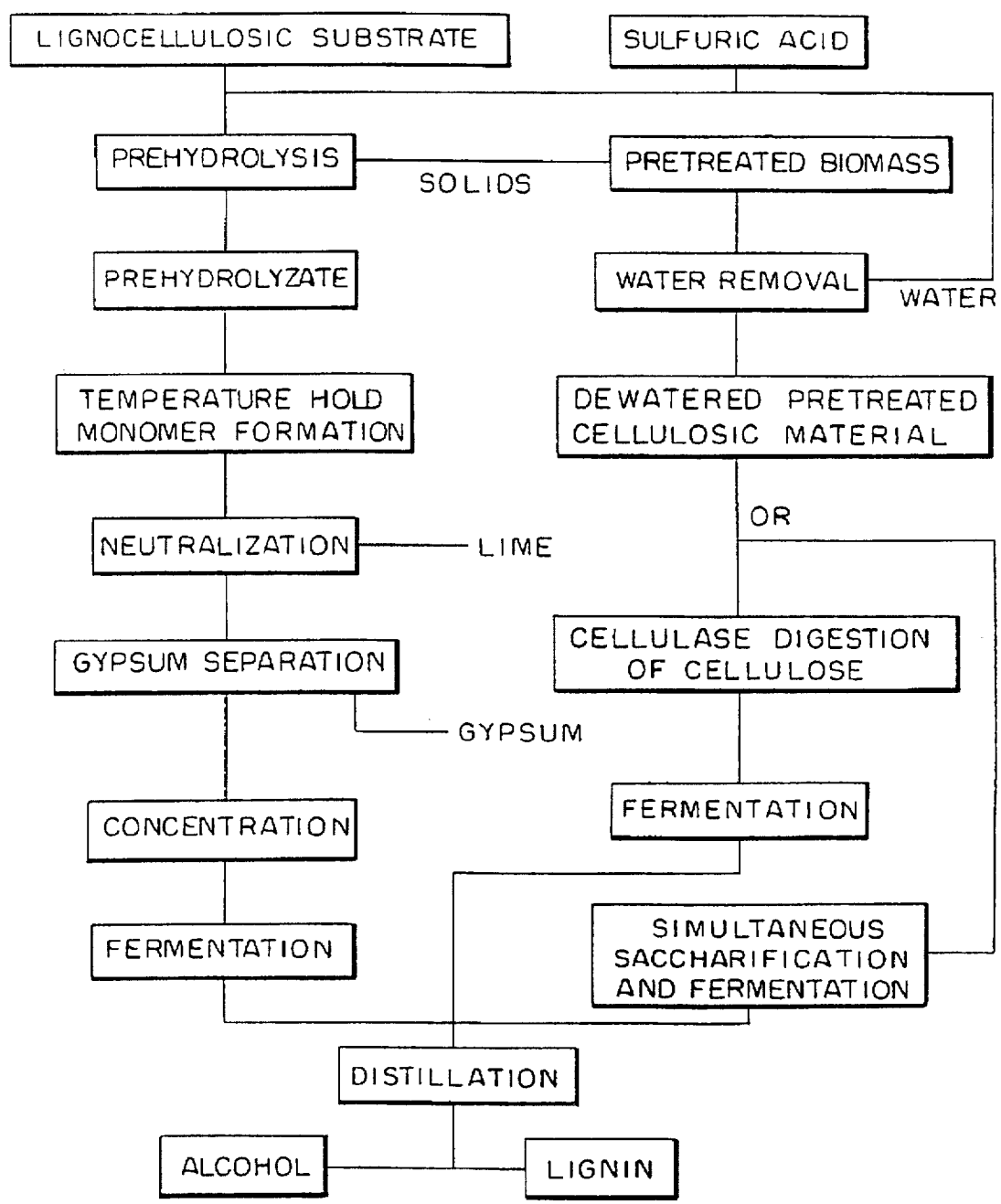
FIG. 1 is a flow chart of the entire process.

Prehydrolysis of lignocellulose involves at least the partial separation of hemicellulose and/or lignin from cellulose so that a more purified cellulose is produced. Prehydrolysis is generally performed by the action of chemicals, particularly chemicals which change the pH, heat and water. Depending on the conditions, different components are separated at different rates. Furthermore, depending on the composition and nature of the particular lignocellulosic substrate, different combinations of conditions will be needed.

In the present invention, the different components liberated from the lignocellulosic solids may be continuously removed under a single set of conditions, plural sets of conditions or under constantly changing conditions. This is performed by a process and apparatus novel to the field of lignocellulose prehydrolysis.

While applicants do not wish to be bound by any particular theory, they believe that the solubilized lignin and breakdown products are more easily separated from the solid lignocellulosic substrates when the composition is hot, i.e. at the temperature used during prehydrolysis. When the composition is allowed to cool after heat and chemical prehydrolysis treatment and before washing the solid material, less hemicellulose and lignin are removed. It appears that the degraded or partially degraded hemicellulose and lignin precipitate or recondenses on the lignocellulosic substrate as it cools and is not easily washed away. Regardless of any particular theory, less separation is noticed.

During the partial removal of hemicellulose and lignin, it is believed that "pores" or the like are created in the hemicellulose/lignin coating which, in later steps, allows cellulase to enter and digest the cellulose. As more lignin and hemicellulose are removed, the "pores" are larger and allow greater contact between cellulose and cellulase. This is believed to be the cause of the greater digestibility noticed in the present invention.

The present invention utilizes a flow-through system where fluid moves with respect to the solid lignocellulose. The lignocellulose solids may be stationary, travel in a counter-current or cross-current fashion. It is even possible for the system to use a co-current or stationary system which is agitated. One typical design is a percolation reactor. One can perform a solid-liquid separation in the flow-through system by using a screw-like device to cause the separation continuously during or at the end of prehydrolysis. Important to the process is the movement and removal of fluid during the prehydrolysis to separate soluble products as they are released from the solid lignocellulosic residue.

Fluid need not be flowing constantly, but may be pulsed or stopped for a period of time, but it does need to move at least part of the time before the end of the prehydrolysis process. Alternatively, a pulsed system may blow air or other inert gas through the system to help push out the prehydrolyzate. An air pulse may also provide an overpressure or simply to agitate the system.

A continuous prehydrolysis reactor may also be used. Such a reactor would have lignocellulosic material driven through the reactor while fluid is passed through the material, typically in a counter-current or cross-current manner. For example, if the prehydrolysis reactor is in the configuration of a column, the lignocellulosic material may be augured into the bottom of the column and removed from the top while fluid containing the degrading compound(s) is added at the top and passes through the biomass to be removed at the bottom. The reverse configuration is also possible. Alternatively, the lignocellulosic substrate may be driven laterally while fluid is applied on top and allowed to percolate down to be removed at the bottom.

One advantage of the flow-through design is that a much higher percentage of xylose can be recovered from the prehydrolyzate. This system can recover over 90% of the xylose, galactose, manose and arabinose whereas previous prehydrolysis systems with one set of conditions recover only 60–80% of the hemicellulosic sugars. Furthermore, radically different amounts of lignin are removed. Previous acid prehydrolysis removes about 5% and at most about 15% of the lignin. By comparison, the acid prehydrolysis of present invention removes at least 20% of the lignin.

The duration of the prehydrolysis process is defined as the period of time when the lignocellulosic material is exposed to a predefined temperature or temperatures and chemical concentration or concentrations. While passing fluid by the solid lignocellulosic material throughout the prehydrolysis period is preferred, one could pass fluid through the reactor only once immediately before the end of the prehydrolysis step. Such a variation is exemplified below.

It is recognized that certain components are easy to hydrolyse whereas others are hard to hydrolyse. Degradation of the soluble products before their removal is not necessary nor particularly desired. Plural or continuous passages of fluid may be preferable, depending on the composition of the lignocellulosic substrate, for the removal of various components as they are solubilized.

It is also recognized that at different times during the prehydrolysis, the composition of the resulting liquor may vary. This is particularly likely if different physical and chemical conditions are used during the prehydrolysis step. Accordingly, different portions of the prehydrolyzate liquor stream need not be mixed together, but rather the liquor stream at one time may be diverted to a different additional treatment from another liquor stream. For example, if xylose monomers, xylose oligomers, hexose and lignin predominate in different streams, one may wish to fractionate the prehydrolyzate and further treat the xylose oligomers outside the prehydrolysis reactor to hydrolyse them. Further, different sugars may be sent to different fermentations as different microorganisms can utilize or prefer different sugars. Likewise, lignin predominant fractions may be discarded, subjected to further treatment or dewatered and burned.

In the simplest situation, a reactor contains a fluid inlet at one end and a fluid outlet at the opposite end. Lignocellulosic material is added to the reactor and fluid is passed through it. One or both of the fluid connections may be covered by a screen, frit or other means for retaining lignocellulosic substrate in the reactor. The lignocellulosic material may be prehydrolyzed in a batch mode, semicontinuous or fully continuous manner. The solids entrance and/or exit (which may be the same) are usually different from the fluid inlet and outlet.

Numerous variations on the basic design are possible, the important feature being the passage of fluid through or across the lignocellulosic material during prehydrolysis. For example, solid lignocellulosic material may be continuously added and continuously withdrawn from the system. Alternatively the solids and liquids may pass in a counter current fashion by having the liquids being pumped through or by a moving solid material. The action of gravity or floatation may also effect movement of either the solid or liquid. Artificial means such as a screw, moving screens or pumped air bubbles may also be used to effect movement. The orientation of the reactor and direction of fluid flow is not critical and gravity may assist in moving either the fluid or the solid lignocellulosic material.

Types of flow-through reactors include percolation reactors, screw-type reactors, gravity flow tower reactors, spray and draining reactors, washing reactors and a number of other variations of solid/liquid contacting and separation systems. The term "flow-through reactor" is intended to cover all of these variations as they all retain solids in a zone while liquids flow out of the zone containing the solids and thereby carry hydrolyzed compounds.

The lignocellulosic material is preferably ground before being placed in the reactor. If the nature of the lignocellulosic material is such that it will brake down when mixed before of inside the prehydrolysis reactor, then grinding is not necessary. The particle size is not critical but generally, the smaller the particle size, the faster the prehydrolysis will occur. Smaller particles also can form a tightly packed bed which will allow less channeling of fluid flow through the bed. Further, smaller particle sizes inherently provide more surface area for cellulase to attack and degrade cellulose after prehydrolysis. On the other hand, particles which are too small may form a dense mat which is difficult for fluid to flow through at an acceptable rate. Very small particles are also difficult to retain in the reactor, may require the use of a fine screen or frit with its increased cost and reduced flow rates and very small particles may tend to clog the pores of any retaining means.

Appropriate particle sizes vary with the feedstock and its inherent physical properties. Particle sizes appropriate for ground wood are in the range of about 0.1 mm to 30 mm preferably in the range of 0.5 mm to 4 mm. Other materials may be larger or smaller depending on the particular materials, particularly those having at least one thin dimension such as paper or straw. If one relies on the effects of gravity or floatation to cause movement of the solid lignocellulosic material with respect to the liquid, then particle size may need to be adjusted appropriately to permit solid/liquid movement in the time period of the prehydrolysis. Optimum sizes will depend on the particular lignocellulosic material used and the reactor size and construction and are readily determinable by routine experimentation.

The lignocellulosic substrate may consist of hardwood, grasses, softwood, waste paper and pulp, municipal wastes, agricultural wastes such as straws, corn cobs, corn stover, biomass of all types, etc. and mixtures thereof. The choice of lignocellulosic substrate will depend on the availability and cost of lignocellulosic materials.

In the present invention, the reactor generally may have a solids content of between about 5 and 50%, preferably about 8–30%, when the solids are present with the liquid at the end of the prehydrolysis. The higher solids content are generally more desirable but the concentration is limited by the designs of the reactor and the need for fluid to flow throughout the solids. At the beginning of the prehydrolysis, the solids content may range from 0 to 100% by weight as the reactor may initially contain only the lignocellulosic solids or the degrading fluid.

To prehydrolyze the lignocellulosic substrate, a degrading compound is added to the substrate either before, simultaneously or after loading the reactor with substrate. The degrading compound may directly degrade the lignocellulose substrate or indirectly degrade it by being converted into an acid or alkali or by interacting with lignocellulose so that it is more susceptible to the effects of acid or alkali.

The degrading compound to effect prehydrolysis may be either acid or alkali. Both strong and weak acids and alkali may be used provided that they attain the desired pH. The degrading compound may be in either solid, liquid or gaseous form. Generally, at least some water will be present during at least part of the prehydrolysis.

Representative inorganic acids include: sulfuric, sulfurous, nitric, hydrochloric, carbonic, hydrofluoric, hydrobromic, phosphoric, boric and oxy acids. Representative organic acids include: formic, acetic, pyroligneous, oxalic, malic, benzene (or other aromatic)-sulfonic, trichloroacetic, trifluoroacetic, carboxylic acids and polymers with organic acid moieties. Representative gaseous acids include: sulfur dioxide, sulfur trioxide, carbon dioxide, chlorine, phosgene and $NO_x$ where x is from 0.5 to 4. Representative gaseous alkali include: ammonia. Representative alkali include: metal hydroxides and ammonium or metal oxides, sulfates, bisulfates, sulfites, bisulfites, carbonates and bicarbonates, $P_2O_5$, urea, guanidine, amino containing compounds, salts of weak acids and polymers containing salts of weak acids. The preferred metals are alkali and alkaline metals to yield alkali such as sodium hydroxide. Representative materials to form acids include: metal halides, e.g. aluminum chloride, copper chloride, zinc chloride, tin chloride, titanium chloride, nitrophenol and chlorophenol. Representative materials to form alkali include: zinc, iron (II) oxide and hydroxy salts. Hydrates of any of these compounds which form are also included.

Each category, as well as each compound or combination of categories or compounds, has inherent advantages and disadvantages. Cost considerations and the composition of the lignocellulosic material are generally controlling. However, certain ones have inherent advantages. For example, alkaline treatments are generally believed to be more advantageous at solubilizing lignin whereas acidic treatments are generally thought to be better at solubilizing hemicellulose. Contrary to previous belief in the prior art prehydrolysis, extreme pH is not needed with the present invention. There is no particular advantage to using a strong acid or alkali from a pH standpoint. Degrading compounds which provide nutrients or cause nutrients to form for a later fermentation have certain advantages as these nutrients will not need to be added later.

Gaseous degrading compounds have distinct advantages and disadvantages. Gases generally will diffuse into the lignocellulosic material faster, thereby permitting a faster reaction or the use of larger substrate particles. Gases also may be easier to handle and require less demanding apparatus. Corrosion of the apparatus is a problem with both gas and liquid degrading agents but should be less of a problem with gasses. On the other hand, these gases tend to be poisonous and therefore avoidance of leaks is a major concern.

Using gaseous degrading compounds also raises the issue of how one is to obtain liquids. To do so, one may add very hot water to the system to wash away the degradation products. Alternatively, steam may be pumped in which will condense to provide the liquid.

Alternatively steamed lignocellulosic material can produce its own acids or alkali in situ from endogenous acidic or alkaline materials, e.g. uronic acid and acetic acid. Combinations used separately or mixtures of acidic or alkaline chemicals may be used. One may even use combinations from different categories of materials such as sulfuric acid and carbon dioxide.

In this patent application, the pH altering chemicals are referred to as acids or alkali. It should be appreciated that compounds which buffer the pH at acidic or alkaline ranges are also considered acids or alkali.

An oxidizing compound may also be added to aid in the degradation of components such as lignin. Examples of oxidizing agents include peroxy compounds (e.g. hydrogen peroxide) or peracid compounds. Other pretreatment chemicals may also be used such as salts or metal chelating agents.

The concentration(s) of the chemical agents to use will depend on a number of factors such as the chemical composition or the lignocellulosic material. Additionally, the water content and the inherent buffering capacity of the substrate also regulate the concentration and amount of degrading compound to add.

For the example of a liquid acid, such as sulfuric acid, being used as the degrading fluid for prehydrolysis, the percolation reactor described above may be filled with lignocellulosic substrate and relatively mild conditions used to acid prehydrolyse the substrate. The conditions include 90°–240° C., preferably 120°–180° C. at a pH of 1.0–5.5 and for 10 minutes to 2 hours. The liquid drawn off is optionally further treated to hydrolyse any xylose oligomers. It should be noted that the pretreatment process simply removes the hemicellulose from the solids, prehydrolysis does not necessarily completely hydrolyse the oligomers. The resulting solid residue has 20–50%, preferably 30–50% of the Klason lignin removed by the prehydrolysis. Almost all of the hemicellulose (>90% xylan removal) and relatively little (up to 25%) of the cellulose is removed by such a treatment. The resultant residue is very digestible by cellulase.

One representative example of a gaseous acid for lignocellulose prehydrolysis is carbonic acid. This acid can produce prehydrolyzates in the pH range of 2–7 with 3–5 being preferred. Carbonic acid may be prepared before addition to the percolation reactor or carbon dioxide may be injected into the reactor to prepare carbonic acid in situ. Conditions include a temperature range of 140°–240° C. with sufficient pressure for the water and carbon dioxide to remain in liquid form.

The liquid drawn off during prehydrolysis and further treated to hydrolyse xylose oligomers may then have its pH altered simply by releasing the pressure and allowing carbon dioxide to volatilize. The pH adjusting process may be encouraged by agitation, bubbling an inert gas through the prehydrolyzate or adding an alkaline material. The carbon dioxide release at this point and carbon dioxide produced by fermentation may be used to prepare additional carbonic acid for prehydrolysis of additional lignocellulosic substrate.

Without the flow-through reactor design, utilization of carbonic acid would not be feasible. In closed systems, if carbonic acid were used it would not be effective for at least one reason. Closed systems require a lower pH than can be achieved with carbonic and other similar weak acids.

Another representative gaseous acid for lignocellulose prehydrolysis is sulfur dioxide. After a lignocellulosic substrate is placed in the percolation reactor, sulfur dioxide is pumped into the reactor and allowed to penetrate the lignocellulosic substrate. Steam or liquid water is then pumped into the reactor and sulfurous acid is formed in situ. The remainder of the process and conditions are the same as for the acidic prehydrolysis described above.

Alternatively, the reactor may already contain lignocellulosic substrate and water and then the sulfur dioxide is sparged into the reactor. The prehydrolysis conditions of temperature and pressure may be obtained before or after sulfur dioxide addition.

To further the acidic pretreatment, oxygen and/or another oxidizing agent such as permanganate may be present to convert sulfur dioxide to sulfur trioxide so that sulfuric acid will later form. A catalyst may be added or may be part of the percolation reactor itself to convert sulfur dioxide to sulfur trioxide. Suitable catalysts include platinum or vanadium oxide. It should be noted that this reaction along with the action of sulfur dioxide/trioxide forming dilute acid are exothermic, thereby producing some of the heat necessary for prehydrolysis.

An additional advantage of employing a solid catalyst is that it provides physical support to the particles of lignocellulosic material. Certain lignocellulosic substrates such as newsprint tend to agglomerate or mat which prevents the even flow of gas or liquid through the lignocellulosic material. Furthermore, fluid which does flow through such a mass tends to channel, thereby causing a drop in pressure and an inefficient and non-ideal distribution of fluids in the reactor.

The use of physical support materials in the reactor is not limited to solid catalysts. Inert particles also may be used to prevent agglomeration and mat formation in the reactor. Suitable inert particles include, glass beads, numerous refractory materials and coarser lignocellulosic material.

Because gases are handled differently from liquids, the percolation reactor apparatus may be modified to accomplish the necessary handling of materials. Furthermore, different degrading materials may require different control mechanisms and impart different requirements for maintaining the chemical inertness of the apparatus. These requirements are well known and thus it would require only routine optimization to adapt the percolation reactor to any specific degrading compound(s).

A representative liquid alkaline material is sodium hydroxide. The alkali can produce a pH of 7–14+ and prehydrolysis may occur from ambient temperature (about 10°–30° C.) to 250° C. The remainder of the process is the same as for acid prehydrolysis except for altering the pH toward neutral will require an acidic material.

A representative gaseous alkaline gas is ammonia. This material also has the advantage of constituting an essential nutrient in a later fermentation. The conditions are the same as above and the equipment may need modifying for gaseous acid compound(s) as noted above.

The liquid flow volumes through the reactor are preferably low in order to keep the concentration of removed sugars high. Generally, the entire flow volume will range from about 1 to 5 total void volumes, preferably about 2 void volumes. While this may produce about twice the liquid of a closed prehydrolysis system, the sugar concentration may be roughly the same after hydrolysis of oligomers because significantly more sugar is removed by the present invention. For example a typical batch prehydrolysis system may produce a liquor having about 4–5% sugar concentration which after washing produces about 3% sugar concentration. By comparison, the present invention may also produce about 1–4% sugar concentration in the liquor.

The pressure during prehydrolysis may be simply the existing pressure when heating aqueous solutions to the desired temperature or slightly more than the pressure generated from water vapor at the particular temperature (steam pressure). The prehydrolysis reaction occurs primarily in a liquid phase and at least at the end of the prehydrolysis reaction, the degrading fluid is to be a liquid. High overpressures are neither necessary nor particularly desired.

The duration and temperature of the prehydrolysis step will vary depending on the lignocellulose substrate. Furthermore, the composition of the prehydrolyzate fluid eluting from the reactor will vary depending on the substrate used. Generally conditions are optimized so that cellulose is not substantially degraded by prehydrolysis. This does not mean that no glucose will be removed from the lignocellulose. Hardwoods undergoing prehydrolysis will typically loose about 5 to 25% glucose during prehydrolysis. Softwoods typically will loose more, in the range of about 10 to 30% glucose during prehydrolysis.

Prehydrolysis may end with a pulse of water to wash the residue and remove degrading compounds from the solids. The wash water may be recycled to the prehydrolysis reactor by adding make-up dilute acid or alkali or it may be added to the prehydrolyzate liquor. When this technique is not used or is insufficient to adjust the pH to an acceptable range for cellulase, a small amount of neutralizing solution or buffer may be added to adjust the pH. This step may be performed in the prehydrolysis reactor or after the solids have been removed. The residue is particularly well adapted to enzymatic digestion by cellulase at this stage.

The liquor from the prehydrolysis reactor contains some soluble pentose and hexose, lignin and oligomers of pentoses. The oligomers are then hydrolysed to monomers, or at least to dimers or trimers, by any conventional technique. The simplest may be to simply hold the prehydrolyzate liquor at the prehydrolysis temperature in a holding vessel. Since this temperature may be too high, the liquor may be flashed by releasing the pressure in the holding vessel. Conditions in the holding vessel are such that oligomers are hydrolyzed while degradation is minimized. Hemicellulases are also known and may be used alone or in combination with the holding treatment if so desired.

The conditions during the temperature hold may be used for other purposes in addition to hydrolyzing xylose, or other sugar, oligomers to monomers. For example, the conditions may be controlled to enhance recondensation or precipitation of lignin. Precipitated lignin is easily removed and may be used to produce other chemicals, used in or on soil as a mulch etc. or burned as fuel.

Oligomers of xylose are generally not readily fermentable by most microorganisms. For example, ethanologenic strains of *Klebsiella oxytoca* can utilize xylose dimers and trimers but not oligomers of xylose with higher degrees of polymerization. See Burchhardt et al, Applied and Environmental Microbiology 58:1128–1133 (1992).

After sufficient hemicellulose has been hydrolysed in the hydrolyzate liquor, the pH of the fluid is adjusted to a pH acceptable for fermentation. If the degrading chemical is sulfuric acid, the preferred pH adjusting compound is calcium hydroxide or calcium oxide. This material not only neutralizes the sulfuric acid but it produces gypsum, its half hydrate or other forms, which is insoluble in water. The precipitated gypsum is then separated to remove it from the process. The temperature is at least about 90° C. and preferably is at least about 100° C. during the separation unless the fluid is under pressure. Higher temperatures under pressure such as 120° C. and above or the prehydrolysis or temperature hold temperatures may also be used. Thus, this neutralization and gypsum removal technique is broadly applicable to any chemical process.

Gypsum, unlike most compounds, is less soluble in the aqueous solution at higher temperatures than at room temperature. Separation may be preformed with a centrifuge, a filter or simply allowing the solid gypsum to settle in a settling vessel. Therefore, pH adjustment and/or at least separation of gypsum is preferably performed when the fluid is hot. This technique may also be applied to the neutralization of other sulfuric acid solutions such as that produced by acid hydrolysis of cellulose. The gypsum may be recovered as a useful chemical such as in the production of plaster of paris.

Previously, gypsum formation has resulted in fouling and numerous difficulties downstream. For that reason, previous prehydrolysis techniques have used cocurrent reactors as a way to reduce the problems with gypsum coating and clogging the apparatus. The present invention more effectively removes gypsum and therefore avoids previous problems and permits one to use a different apparatus.

If the degrading chemical is carbonic acid, the pH adjustment occurs in a different manner. Instead of adding a chemical, one can simply reduce the pressure in the system and carbonic acid will be removed by volatilizing carbon dioxide. The carbon dioxide may be recovered from this stage and from the fermentation and reused earlier in the process to prepare carbonic acid. This technique has certain advantages in avoiding or reducing the cost of degrading and neutralizing chemicals. To further aid in carbon dioxide removal, an alkali may be added to the prehydrolyzate liquor and/or an inert gas may be pumped through the fluid to encourage removal of carbon dioxide gas.

After the pH has been adjusted to an acceptable range, the concentration of sugars in the prehydrolyzate liquor may be measured. If the concentration is too high, the liquor is diluted. If the concentration is too low, the solution is concentrated by any standard dewatering technique which will not adversely affect the sugars. The sugars may be recovered and purified or utilized without further purification being necessary.

The liquor is then ready to be fermented to an organic compound such as an alcohol (ethanol, etc), a ketone (acetone, etc.), a carboxylic acid (butyric acid, etc.) etc. The liquor may be supplemented with other nutrients, its physical and chemical properties (pH, temperature, concentrations, etc.) measured and modified if necessary and fermented by a microorganism capable of utilizing the sugars in the liquor to produce a desired organic compound. This technique is known per se and is thoroughly described in the fermentation art.

After the fermentation has produce the desired organic compound, the compound is removed from the fermenter by techniques known per se such as distillation. The fermentation and removal each may be continuous, batch or fed-batch.

The solid residue remaining after prehydrolysis may be removed and have its pH adjusted in a similar manner to a pH suitable for cellulase digestion of cellulose. Alternatively, one may wash the solids with water, to reduce or eliminate the need for neutralization. This washing step may be performed at the end of prehydrolysis while maintaining the temperature and pressure, or it may be performed after prehydrolysis has been completed. The wash water may be reused, discarded or added to the prehydrolyzate liquor as desired. The pH and solids content may be measured and adjusted to optimize for cellulose digestion by cellulase.

By using this percolation pretreatment system and "washing out" hydrolyzed acid-labile lignin, a substrate is produced which has been significantly delignified and is very amenable to enzymatic saccharification using a cellulase enzyme system. A "significantly reduced amount" of lignin constitutes the amount needed to enhance digestibility of the lignocellulosic substrate by the enzyme cellulase. The "enhanced digestibility" is enhanced over the previous techniques resulting in 5 to 15% removal of lignin. For the purposes of this patent application, a "significantly reduced amount of lignin" is greater than about 20% removed.

Cellulase is then added to the pH adjusted residue and the cellulose digested to sugars. This process is carried out in a manner known per se. Any of the known cellulases or cellulase complexes may be used. Typically the digestion will be carried out for one to three days at a temperature optimal for the cellulase. The sugar containing solution is separated from the residues by, for example, filtration, sedimentation or centrifugation. The sugar solution may be recovered as sugars or it may be fermented in a manner known per se to produce a desired organic chemical.

The fermenting microorganism may be the same as was used to ferment the hydrolyzate liquor. However, because cellulose digestion primarily produces glucose, a much wider variety of microorganisms may be used to produce an even wider assortment of organic compounds. The residue digest may be fermented in any manner known per se to utilize glucose. If so desired, the residue digest may be mixed with the hydrolyzate liquor before or during fermentation.

As an alternative to separate cellulase digestion and fermentation, both reactions may occur simultaneously in "simultaneous saccharification and fermentation", a technique known per se. Any fermentation which is operable in conditions suitable for cellulase is acceptable. The conditions and concentrations in simultaneous saccharification and fermentation (pH, temperature, etc.) may be measured and adjusted to be optimized for either saccharification or fermentation or for overall optimization. The conditions may be changed as the process progresses. The prehydrolyzate liquor may be added to the simultaneous saccharification and fermentation if desired.

One may combine the fermentation of the prehydrolyzate liquor and the fermentation of the sugars from the solids simultaneously. This combination has certain advantages and disadvantages. Whether to use a combined fermentation would depend on the composition of the feedstock and the economics of the particular plant and local area. Advantages include the use of fewer fermentation vats. Also, cellulase would be carried over into the fermentation and many cellulase preparations contain xylanase activity. This would serve to degrade any residual oligomers of xylose. Disadvantages include the need for specialized microorganisms for fermenting pentoses whereas glucose can be fermented by many microorganisms such as yeast.

Because the prehydrolysis used in the present invention removes a greater amount or percentage of lignin and hemicellulose from the lignocellulosic material, the residue is more easily digested with cellulase. This improved result is reflected by four desired properties.

With less lignin and hemicellulose binding to the cellulose fibers, greater contact between cellulase and cellulose is achieved. This is reflected in a greater speed of digestion. Secondly, because less cellulose is hidden behind a layer of lignin and hemicellulose, a higher overall digestibility of the substrate and higher yield of sugar is observed. Thirdly, cellulase binds to lignin. With less lignin present, less cellulase binds to lignin and therefore the cellulase added appears to have a greater activity in use. Accordingly less cellulase is needed to perform the digestion. Fourthly, the significantly reduced lignin content remaining in the solid residue translates into reduced lignin in the fermenter. This permits one to use a smaller fermenter, less power to mix it and results in less lignin clogging up all of the down stream systems. All of these advantages result in significant cost reductions in the overall process of producing sugars or fermented organic compounds from lignocellulose.

Unlike previous prehydrolysis techniques, the present invention permits one to use more than one set of conditions during a single prehydrolysis. If fluid is passed through the solids continuously or at least at the end of each set of conditions, then the prehydrolysis may be optimized to solubilize different materials at different times. For example, with the previous prehydrolysis systems, one would need to end the prehydrolysis, remove the material from the reactor, wash the liquid from the solids, return the solids to the same or a different prehydrolysis reactor and perform a separate prehydrolysis under different conditions to obtain a second liquid fraction. With a flow-through reactor of the present design, one can change the temperature, pressure, pH and chemical additions during the same prehydrolysis step while removing different fractions of solubilized liquid.

Different fractions of liquid produced by a varying prehydrolysis may be post-treated differently and optimized for their separate chemical composition. Closed prehydrolysis systems do not permit such a variation in conditions with removal of the fluid between different conditions. PH would be almost impossible to control or vary in a closed system.

The present invention includes the changing of at least one condition at least once during a single prehydrolysis step. The prehydrolyzate liquor is withdrawn during or at the end of each set of conditions. The condition(s) may be changed any number of times and may even be continuously changed.

Using plural conditions during prehydrolysis has at least three distinct advantages over conventional prehydrolysis. First, different lignocellulosic substrates may be treated differently as appropriate to optimize results. This is particularly advantageous when one considers a continuous addition of lignocellulosic substrate to the prehydrolysis reactor. The substrate may be analyzed for its physical properties and chemical composition as it arrives and optimal prehydrolysis conditions adjusted accordingly.

Secondly, fluid travel in a flow-through reactor cannot be ideal even though this is desirable. While experiments exemplified below show near ideal distribution of fluid throughout the reactor, in practice it may be very difficult to maintain an ideal distribution. Accordingly, it is desirable to change the conditions in the prehydrolysis reactor to compensate for non-ideal conditions. The present invention permits such a change by sensing conditions inside the prehydrolysis reactor and liquid or solid products leaving the reactor and from that data adjusting the conditions in the prehydrolysis reactor to compensate for non-ideal distribution.

Thirdly, one can periodically or continuously monitor the products or conditions inside or emitting from the prehydrolysis reactor as a measure of the effectiveness of the prehydrolysis reaction. Should the measurements vary from what is considered optimal, the conditions within the prehydrolysis reactor may be changed accordingly. This type of system lends itself to constant monitoring and control by a feedback loop with a computer.

The harshness or severity of the prehydrolysis treatment is a function of the temperature, time, pressure and concentration and type of chemical, particularly the pH generated by the chemical. The combination of these features are critical to the degree of prehydrolysis and a decreased value for one can frequently be compensated by an increase in one of the other parameters. The result is the kinetic concept of a combined severity parameter. This idea is certainly not new to chemical engineering as time and temperature have long been recognized as adjustable in opposite directions to usually yield the same result.

In the field of lignocellulosic prehydrolysis and fractionation of wood components, elaborate equations for calculating a "combined severity parameter" have been used. See Chum et al, Applied Biochemistry and Biotechnology 24/25: 1–14 (1990). The combined severity parameter calculations have even been used to justify radically different parameters such as using simply water, presumably close to pH 7, with a very high temperature and pressure. See Mok et al, Ind. Eng. Chem. Res. 31(4):1157–1161 (1992).

A significant benefit from the present invention is the use of less severe conditions with a lower combined severity parameter resulting in greater component separation using the method of the invention as compared to previous prehydrolysis techniques. Furthermore, when using a lower combined severity parameter, greater hemicellulose removal and reduced production of unwanted breakdown products (furfural, tars, etc.) was observed as compared to more severe conditions in a simple reactor with separation of liquid after prehydrolysis was completed and reactor cooled.

Another significant advantage to the present invention is the use of a pH which is less extreme. Previous attempts at acid prehydrolysis at 160° C. in a close reactor have required a very low pH. Some have even speculated that a pH above 1.5 is inoperable because of the very long time needed to achieve substantial prehydrolysis at this temperature. With the present invention, a pH in ranges as high as 3–4 at a temperature of 160° C. can produce a digestible solid substrate. Therefore, using a percolation reactor in the process of the present invention has permitted substantially less acid to be required, a greater choice of acids, and less demanding equipment to handle the reaction.

In the present invention, one is even able to use prehydrolysis conditions which are not acceptable for a closed batch prehydrolysis process. Because of the use of less severe conditions, less unwanted degradation products such as furfural and tars are formed during the prehydrolysis. This is particularly advantageous when the results are to be fermented as furfural compounds and tars are toxic to many microorganisms and in sufficient concentrations inhibit fermentation.

The use of less severe conditions provides a number of additional advantages such as using less demanding equipment, numerous cost advantages and most importantly, permits the use of a less extreme pH and permits the use of different degrading compounds. Many of these degrading compounds would not be effective in closed prehydrolysis systems because they do not generate extremely severe conditions.

One example of a particular apparatus which may be used in the process of the present invention is a screw device which conveys solids by drag forces while liquids move in the opposite direction by the forces of gravity. The design may be a conventional intermeshing twin screw device, an Archimedes screw or another screw device which use the action of drag to move the solids and gravity to move the liquids may be used.

This screw device is maintained under prehydrolysis conditions. It may be the primary prehydrolysis vessel or it may simply receive material from a prehydrolysis vessel through its inlet port which was already at least partially prehydrolyzed. The screw device effects counter current solid/liquid separation while the material is under prehydrolysis conditions. Therefore, the screw device performs the same function of a flow-through prehydrolysis reactor without actually pumping any additional fluid into the reactor.

The screw device may be vertical or inclined. The solid-liquid slurry or mixture is added through an inlet port in a barrel of the screw somewhere between the ends. The solid materials are moved to the top while liquids drain to the bottom. Appropriate discharge ports for solids and liquids are provided.

The general construction of similar screw devices is well known and commercially available. Examples include Holstead et al, U.S. Pat. No. 3,859,217 and Duchateau et al U.S. Pat. No. 4,311,673. Screw devices have even been used in enzymatic digestion of materials for ethanol production, Hayes, U.S. Pat. No. 4,326,036 and soaking cellulosic material before digestion in a gas phase, Richter, U.S. Pat. No. 3,532,594. However such screw devices are generally not adapted or able to maintain the conditions appropriate for lignocellulose prehydrolysis which are mentioned above. Furthermore, screw devices have not heretofore been used for solid/liquid phase separation of reaction products in any chemical reactor.

Slots, grooves, dimples and the like may be present on the barrel or screw blades to assist in the conveyance of the solids. The screw blades may also contain pores or screen-like portions which allow liquids to pass through the screw while retaining the solids. To further separate liquids from the wet solids, the top portion of the screw may have threads which become progressively closer so that the solids may be squeezed to force out more liquid as the screw rotates. Wash water may be added to the screw through a port in the barrel at any location, preferably at a level above the inlet port.

Solids finally produced at the top of the screw are transported away by a scraper, auger or the like. Liquids produced at the bottom of the screw are removed. If the screw is maintained under pressure, high pressure pumps may be used to remove the solids and liquids. Alternatively, the solids and liquids may be stored in separate holding vessels until further use. As with the general flow-through reactors described above, it is important for the screw to effect solid/liquid separation while the mixture is still hot.

The invention can be better illustrated by the use of the following non-limiting examples, all of which related to the acid prehydrolysis of lignocellulosic material.

EXAMPLE 1

A lignocellulose containing substrate used in these Examples is Populus eugeneii (hybrid poplar) DN 34 which was provided by the University of Minnesota at Crookston. It was harvested in the fall of 1992, manually debarked, and coarsely chipped using a Formost mobile knife chipper ("Brush Bandit"). The chips were milled further using a laboratory knife mill (Thomas-Wiley laboratory mill, Arthur H. Thomas Co., Philadelphia, Pa.) equipped with a 1-mm rejection screen. Milled material was further separated into a −60 to +80 mesh (0.18–0.25 mm) fraction by using a portable sieve shaker (Tyler Industrial Products, Mentor, Ohio) equipped with USA Standard Testing Sieves. This material constituted the "biomass" for the experiments performed in the examples.

A liquid cellulase preparation used in these Examples (Genencor Laminex cellulase, San Francisco, Calif.), was stabilized by the addition of glycerol and stored at 4° C. until it was used. The specific activity of the enzyme was approximately 64 international filter paper units (IFPU)/mL (22).

$\beta$-glucosidase activity in this preparation was approximately 82 international units (IU)/mL (22). Fungal $\beta$-glucosidase (250 IU/mL [22], Novozyme 188, NOVO Lab Inc., Wilton, Conn.) was used to supplement the cellulase preparation such that the ratio of $\beta$-glucosidase to cellulase was 3:1 in all Examples. The yeast used in the simultaneous saccharification and fermentation (SSF) Examples was *Saccharomyces cerevisiae* $D_5A$. This strain is described in Spindler et al, Biotechnology Letters, 14:403–407 (1992). The remaining chemicals were purchased from national laboratory supply houses. Cellulose powder ($\alpha$-cellulose), used as a control substrate, was obtained from Sigma Chemical Co. (St. Louis, Mo.).

The design of the percolation reactors used in these Examples resembles pressure chromatography columns with valving at both ends and dispersion frit at the entrance followed by a retention frit. A retention frit was also installed at the exit.

The apparatus used included a percolation reactor that was of sufficient dimensions so as to hold enough raw and pretreated biomass for analytical work. A reactor 2 in. (51 mm) in length by 1 in. (25 mm) in diameter was used. The particle size, −60 mesh to +80 mesh (0.18 to 0.25 mm), was chosen to minimize dispersion of the acid catalyst in the flow-through reactor. Before dilute-acid pretreatment experiments could begin, a flow characteristic study was initiated to quantify the flow behavior of the catalyst as a function of temperature and flow rate. Once the flow characteristics were quantified, the pretreatment experiments were conducted. The quality of the pretreated residue was assessed by both enzymatic saccharification and the conversion of the glucan to ethanol by the SSF protocol.

A threaded hole is located at the midpoint of the reactor length through which a thermocouple is installed to monitor temperature. The thermocouple head may be bent to be located at almost any point in the interior of the reactor. For all experimental runs in these examples, the thermocouple head was located at the center of the reactor. Carpenter 20Cb-3 stainless steel was used as the material of construction for the reactor. The dispersion frit (1-in. [25 mm] diameter, 2 micron pore size, made of titanium) and the retention frits (1-in. [25-mm] diameter, 60 micron pore size, made of Inconel) were obtained from Mott Metallurgical, Farmington, Conn. Titanium tubing ($\frac{1}{16}$-in. [1.6-mm] outside diameter×0.03-in. [0.8-mm] inside diameter) used to connect the reactor with other components of the system was obtained from Anspec, Ann Arbor, Mich. The 2-in. [51-mm] bar stock (used for the head plates of the reactor) and the 1-in. [25-mm] ID tubing (used for the body of the reactor), which were both made of Carpenter 20Cb-3 stainless steel, were obtained from Carpenter Technology, Dallas, Tex., and Marmon Keystone, Denver, Colo., respectively. The three-way Hastelloy C valves were obtained from Valco Valve Corporation, Houston, Tex. The third port of the three-way valves was not used for these experiments. The reactor was fabricated and assembled by Falcon Fabrication, Arvada, Colo.

Figure 2:
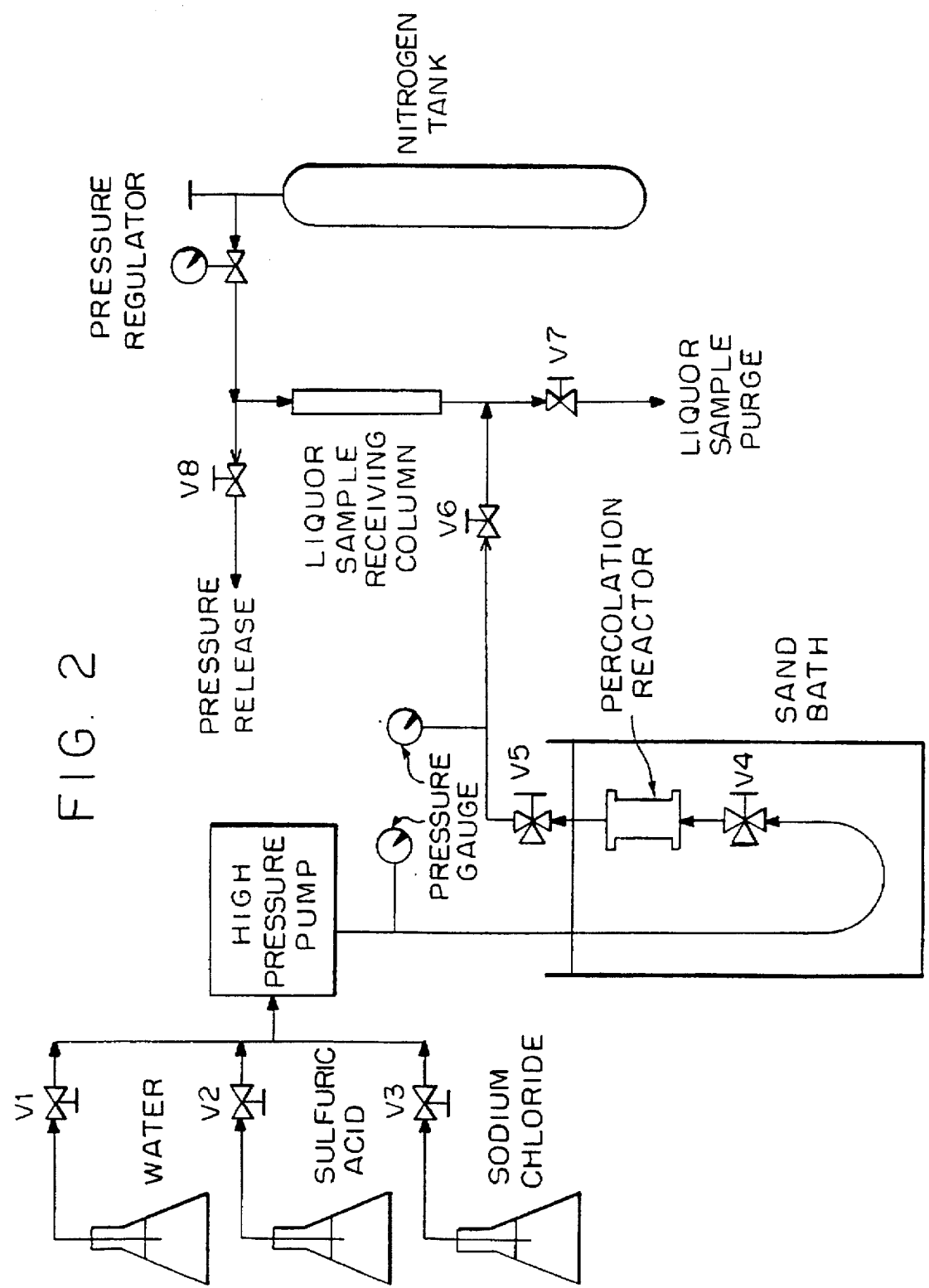
FIG. 2 is a schematic view of exemplary apparatus used in the Examples.

A schematic of the flow system and equipment design is seen in FIG. 2. For all flow characteristic studies and dilute-acid pretreatment runs, the following protocol was used. The reactor was charged with 3.80 g (3.53 g bone dry basis) of ambient-air-dried biomass and the reactor head plates bolted shut. Once the reactor was closed, the inlet line was attached to the water line from a high performance liquid chromatograph (HPLC) pump (Beckman Instruments, model 110B, Fullerton, Calif.) and the exit line was left open to the atmosphere. Water was pumped through the reactor at ambient temperature at 1.1 mL/min for at least 4 h to ensure total wetting of the biomass. The reactor was then submerged in a 90° C. sand bath (SB series General Laboratory Fluidized Bath equipped with a temperature controller, Cat #W3280-3, VWR Scientific, Denver, Colo.) with water being pumped through the reactor at 1.1 mL/min until the center of the reactor reached 88° C. The reactor was then heated for an additional 10 min to allow the trapped air in the wood pores to escape. The reactor temperature was then changed either for flow characteristics experiments or pretreatment experiments as described below.

EXAMPLE 2

The total void volume of a water-saturated, deaerated, packed reactor was determined by quantitatively removing the entire contents of the reactor and immediately recording the weight, followed by drying the reactor contents at 105° C. The weight difference between the wet and dried reactor contents is a measure of the water present in the reactor or of the total void volume of the reactor, which was determined to be 21.4 mL.

In order to define the prehydrolysis time in the reactor, the flow characteristics in the reactor were examined to determine how the observed flow varies from ideal plug flow. The method of residence-time distribution (RTD) determination of Smith et al, Chemical Engineering Kinetics, 3rd. ed. McGraw-Hill, NY (1981), in a homogeneous reactor operated isothermally was employed. In this part of the investigation, conditions (of tracer and temperature) were selected so that reactions did not occur. The RTD method assumes that the linear axial velocity, u, and the tracer concentration are uniform across the diameter. In the packed-bed percolation reactor, It was further assumed that the total void volume is distributed evenly throughout the length of the reactor. Accordingly, the deviation from ideal plug-flow conditions can be determined from the tracer concentration in the effluent in response to a step change in the feed tracer concentration. The governing equation is $$\left(\frac{C}{C_0}\right)_{step} = \frac{1}{2}\left[1 - erf\left(\frac{1}{2}\sqrt{\frac{uL}{D_L}}\frac{1-\theta/\bar{\theta}}{\sqrt{\theta/\bar{\theta}}}\right)\right]$$

where $C$ and $C_o$ are the tracer concentrations in the effluent and feed, respectively; L is the reactor length; $D_L$ is the axial effective diffusivity; $\theta$ is the elapse time after the step change in the feed tracer concentration; $\bar{\theta}$ is the mean residence time; and erf is the error function. See Abramowitz et al, Handbook of Mathematical Functions, 10th printing, National Bureau of Standards (1972). As such, the response in the effluent, $C/C_o$, is a function of $D_L/uL$ (the reciprocal of the Peclet number), and the greater the group $D_L/uL$, the greater the flow in the reactor deviates from ideal plug flow.

For the RTD studies, the reactor was charged with biomass and deaerated as described above. The reactor inlet was connected to the HPLC pump and the exit port was connected to a RI detector (Altex model 156). Three reservoirs were available for liquid flow; 10 mM sodium chloride, deionized water, and 0.4 wt % sulfuric acid. At time zero, either the NaCl or $H_2SO_4$ reservoir was brought on line and replaced the water reservoir for the step-change tracer experiments. A strip chart recorder (Recordall Fisher Scientific, Denver Colo.) was connected to the RI detector, which responded to both the NaCl and $H_2SO_4$ solutions. For the 140° C. tracer studies, the reactor was submerged in a 140° C. sand bath and connected on line through the RI detector with a valve to the receiving column (Omni glass chromatography column assemblies rated at 150 psig [1,030 kPa gauge]) closed. Once the reactor reached 140° C., nitrogen gas was used to charge the receiving column and match the reactor pressure. When the entire system was at equal pressure, the valve was opened. The entire transient response in the reactor effluent after the feed was stepchanged to either NaCl or $H_2SO_4$ was recorded. The experimental reproducability was verified by conducting two runs on two different days using two different biomass packings.

Because of the height to diameter ratio of the reactor channeling could have been a problem if the dispersion frit was ineffective. A control residence time distribution (RTD) experiment was run in which an entrance head plate was drilled out forming a conical shape to allow the entering liquor to disperse over the entire surface area of the biomass. If channeling was a problem, the RTD function for the non-conical head plate would have shown more non-ideal flow characteristics than the drilled out head plate. Experiments revealed this to not be the case. Therefore, channeling was not a problem.

EXAMPLE 3

In this example, a two-temperature pretreatment using a percolation reactor packed with the hybrid poplar wood flour biomass was used. In order to better define the experimental conditions that would give high xylose equivalent yields, a mathematical modeling of the process using the two-temperature pretreatment of hybrid poplar xylan was used. It has been demonstrated through mathematical simulations (See Kim et al, Applied Biochemistry and Biotechnology, (1993) accepted for publication for mathematical modeling) that after the biomass is cooked at temperatures between 135°–150° C. using 0.73 wt % sulfuric acid for residence times necessary to hydrolyse 60% of the xylan, a step-change increase in prehydrolysis temperature of between 25° and 35° C. to hydrolyse the remaining xylan results in maximum yields of xylose in the prehydrolyzate. Furthermore, using 170° C. as the upper prehydrolysis limit, maximum yields of xylose are obtained by using 140° C. as the lower prehydrolysis temperature and residence times of 34 minutes, 20 seconds and 21 minutes, 51 seconds at the lower and higher temperatures, respectively. A total volume of hydrolysis liquor equaling two total voids was calculated to give a maximum xylose equivalent yield. Although the wood substrate used in the mathematical modeling had a slightly different chemical composition than the biomass used in the present examples, the above residence times and temperatures were used in the present protocol and considered to be appropriate.

The reactor was charged with biomass and deaerated as described above. Immediately following deaeration, the reactor was connected to a collection system with the value closed. The reactor was then submerged in the 140° C. sand bath. Once the reactor reached the prehydrolysis temperature, the system was pressure-equalized as described above, 0.73 wt % sulfuric acid was pumped to the reactor at the rate of 8.8 mL/min (linear flow rate of 2.09 cm/min) for 1.5 min (the time for the acid to first appear at the exit end of the reactor), and the effluent liquor discarded (all subsequent prehydrolyzate was collected for analysis). The acid was then pumped at 8.8 mL/min for an additional 2.5 min to totally saturate the reactor with acid (which was determined from flow characteristics studies). The pumping rate was then adjusted to equal just under one total reactor void volume over the desired prehydrolysis time to hydrolyse approximately 60% of the xylan (flow rate=0.62 mL/min for 30 minutes, 15 seconds). The reaction was quenched by pumping water to the reactor at the rate of 8.8 mL/min for a total of 6 minutes, 10 seconds which was the time to completely wash all the acid out of the reactor. The pump was then shut off and the valve closed. With the reactor remaining in the sand bath, the temperature was raised to 170° C., the system pressure was equalized, the valve was opened, and the liquor pumping sequence mentioned above was repeated (except that the pumping rate and time used to send just over one total void volume through was 1.35 mL/min for a total of 17 minutes, 45 seconds). After quenching the reaction as described above, the reactor was cooled to ambient temperature and the solid contents collected in a glass-sintered funnel of medium porosity. The solid residue was then weighed and chemically analyzed; the combined prehydrolyzate (from 140° C. and 170° C. prehydrolyzates) was analyzed for xylose and other components.

EXAMPLE 4

The dry weight of all solids and the ash content of the native feedstock were determined by standard methods (Official Test Methods, TAPPI, Atlanta, Ga.). Lignin and other acid-insoluble components were determined as Klason lignin by standard methods. Moore et al, Procedures for the Chemical Analysis of Wood and Wood Products, (1967) USDA Forest Products Laboratory, Madison, Wis. Acid-soluble lignin was determined by using an aliquot from the Klason lignin filtrate by standard methods. Technical Association of the Pulp and Paper Industry Standard Method T 250, TAPPI, entitled "Acid-soluble Lignin in Wood and Pulp". Uronic acids, acetyl groups, and furfural were determined as described in Torget et al, Applied Biochemistry and Biotechnology 24:115–126 (1990). The carbohydrate composition of biomass solids was determined by a modification of the two-stage sulfuric acid hydrolysis (Moore et al, Procedures for the Chemical Analysis of Wood and Wood Products, (1967) USDA Forest Products Laboratory, Madison, Wis.) followed by determination of monomeric sugars by ion-moderated partition (IMP) chromatography (the slight modification was the use of a 2-h incubation of the substrate in 72 wt % sulfuric acid instead of a 1-h in order to solubilize the glucan completely). The prehydrolyzates (prehydrolyzate is defined as the liquid phase resulting from an acid pretreatment run) obtained from pretreatment experiments had their pH raised by adding calcium carbonate and filtered. The carbohydrates could then be analyzed directly. If the presence of oligomeric sugars was suspected in the neutralized filtrate, the prehydrolyzates were adjusted to 4 wt % sulfuric acid and autoclaved at 121° C. for 1 h (See Moore et al, supra), neutralized, and analyzed by IMP chromatography using Aminex HPX 87XP and HPX-87C columns (Bio-Rad, Richmond, Calif.), deionized water as eluant, and refractive index (RI) detection.

The results of the hydrolysis showed that 13.9% of the glucan was solubilized. Furthermore, 92.0±1.6% of the xylose was recovered and 90–100% of the galactose, manose and arabinose were recovered. The amount of degradation products produced was small. Furfural was 2% of the xylan, hydroxymethyl furfural was 0.4% of the glucan and 0.04% of the prehydrolyzate was acetic acid.

EXAMPLE 5

Figure 3B:
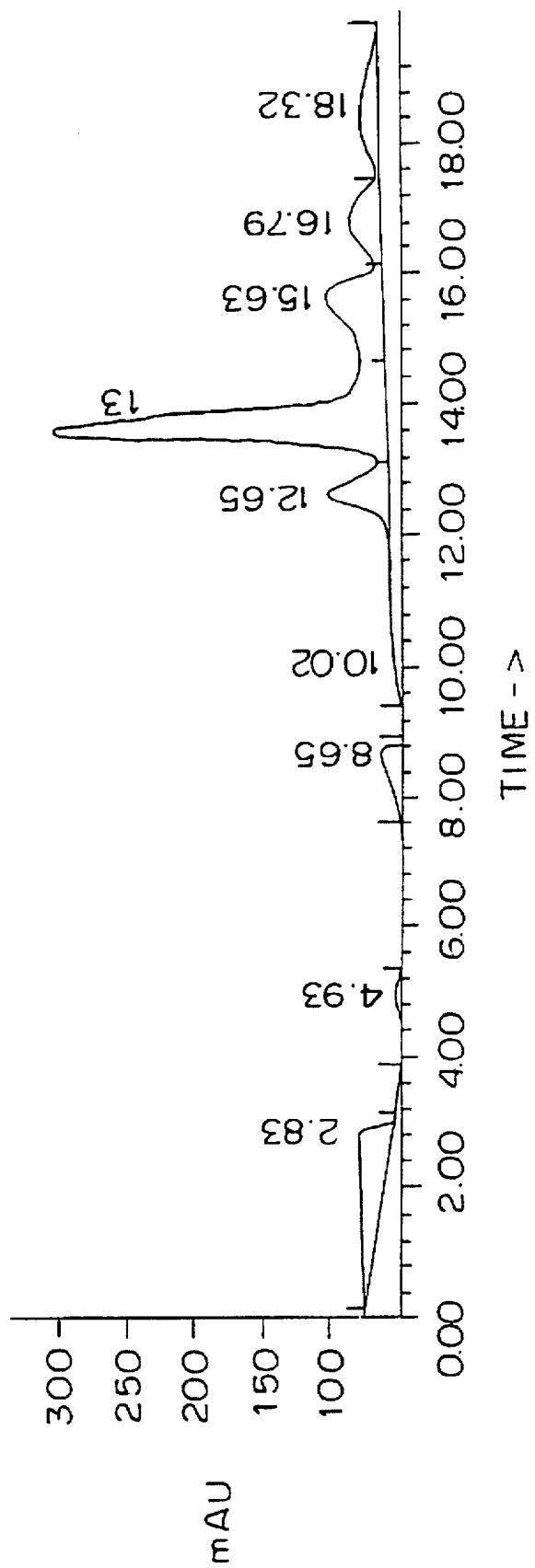
FIG. 3b is the result of HPLC separation of components of the prehydrolyzate after it has been further acid hydrolysed.

The amount of xylose as compared to oligomeric xylose was determined in the prehydrolyzate. A sample of the prehydrolyzate was passed through a HPLC column and the peaks were measured. The results are shown graphically as FIG. 3a. The peak at 13.74 minutes represents xylose which was given a relative height of 180.

The hydrolyzate was hydrolysed with 4% sulfuric acid to hydrolyse all oligomeric carbohydrate to their monomers. A sample of this was passed through the same HPLC column and the peaks were measured. The results are shown graphically as FIG. 3b. The peak at 13.70 minutes represents xylose which was given a relative height of 320.

This data demonstrates that approximately 44% of the hydrolysed xylan in the prehydrolyzate was present as oligomers.

EXAMPLE 6

Enzymatic hydrolysis was performed in batch mode at 50° C., pH=4.8 using a 0.05M sodium citrate buffer, in gently rotated 20-mL glass scintillation vials at approximately a 45° angle as previously described. Grohmann et al, Biotechnology and Bioengineering Symposium, 15:59–80 (1985), Grohmann et al, Biotechnology and Bioengineering Symposium, 17:135–151 (1986) and Torget et al, Applied Biochemistry and Biotechnology, 24:115–126 (1990). Cellulase enzyme loading was approximately 42 IFPU/g cellulose and supplemented with fungal $\beta$-glucosidase at approximately 126 IU/g cellulose. This level of cellulase loading has been shown previously to be at saturating levels of activity when using $\alpha$-cellulose as a standard. See Grohmann et al, Biotechnology and Bioengineering Symposium, 15:59–80 (1985). This is above the IFPU/g cellulose used in the SSF Examples described here and below.

In addition to testing the pretreated substrate for the efficacy of the pretreatment in terms of rates and the extent of enzymatic saccharification, an SSF protocol was used to give additional information on the quality of the pretreated substrate as to its rate and the extent of convertability of its glucan content to ethanol. Extensive research has demonstrated that SSF, the simultaneous saccharification (hydrolysis) of cellulose to glucose and fermentation of glucose to ethanol, improves the kinetics of biomass conversion through circumvention of enzyme inhibition by hydrolysis products, minimization of contamination risk because of the presence of ethanol, and reduction of capital equipment requirements. The kinetics of the process are described by Spindler et al, Applied Biochemistry and Biotechnology 28/29:773–786 (1991).

Shaker flask SSFs were carried out in 250-mL flasks outfitted with stoppers constructed to vent $CO_2$ through a water trap as previously described by Spindler et al, Applied Biochemistry and Biotechnology 28/29:773–786 (1991), with minor modifications. The cellulase preparation was employed at a concentration of 25 IFPU/g cellulose for both the standard $\alpha$-cellulose and the pretreated poplar wood and supplemented with $\beta$-glucosidase at approximately 3 IU $\beta$-glucosidase to 1 IFPU cellulase. This cellulase loading translates into 21.4 IFPU/g native bone-dry poplar hybrid. Ethanol concentrations in the supernatants were measured by gas chromatography as previously described by Spindler et al, supra.

Figure 4A:
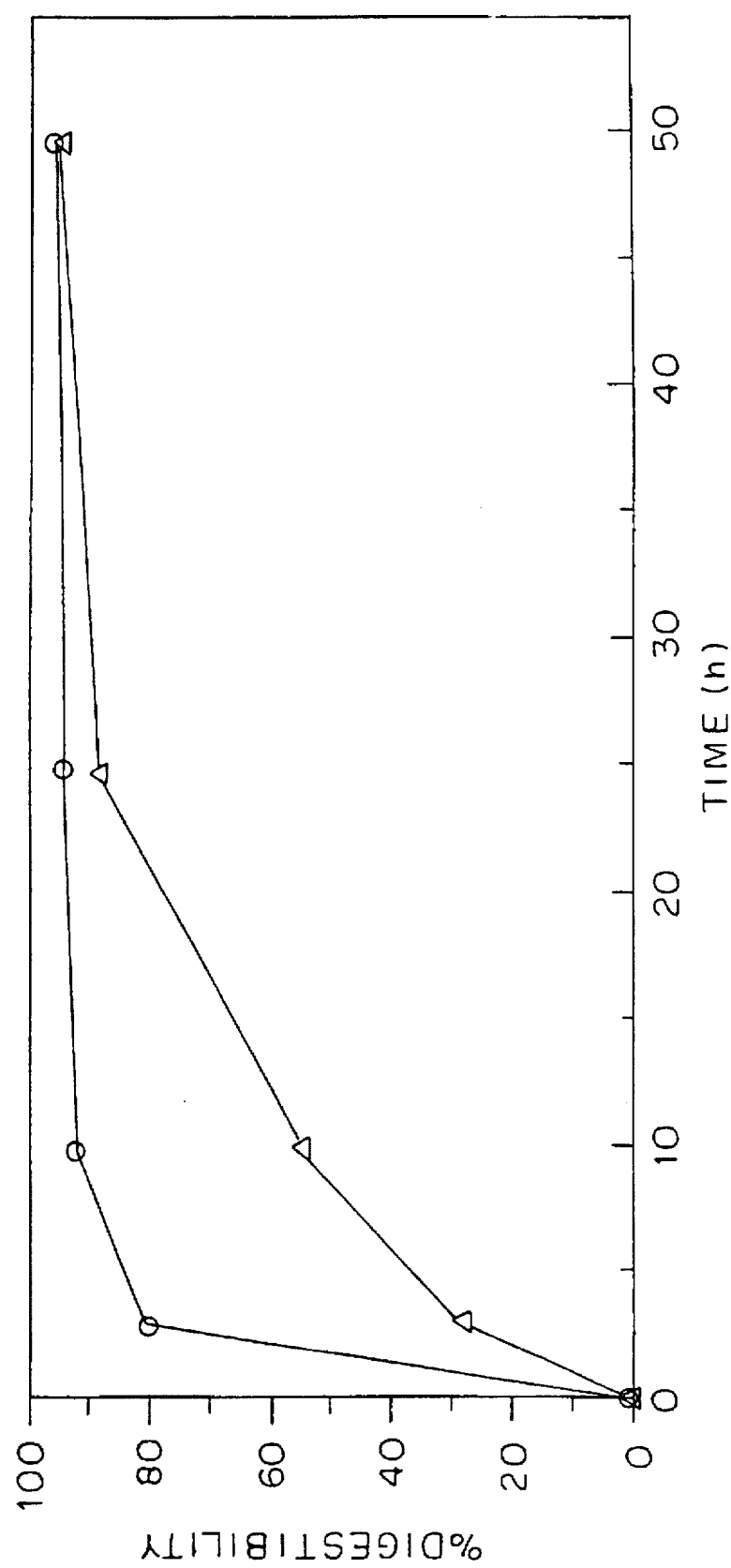
FIG. 4a displays the percentage of cellulose digested by cellulase for the pretreated product of the present invention as circles and for α-cellulose control as triangles.
Figure 4B:
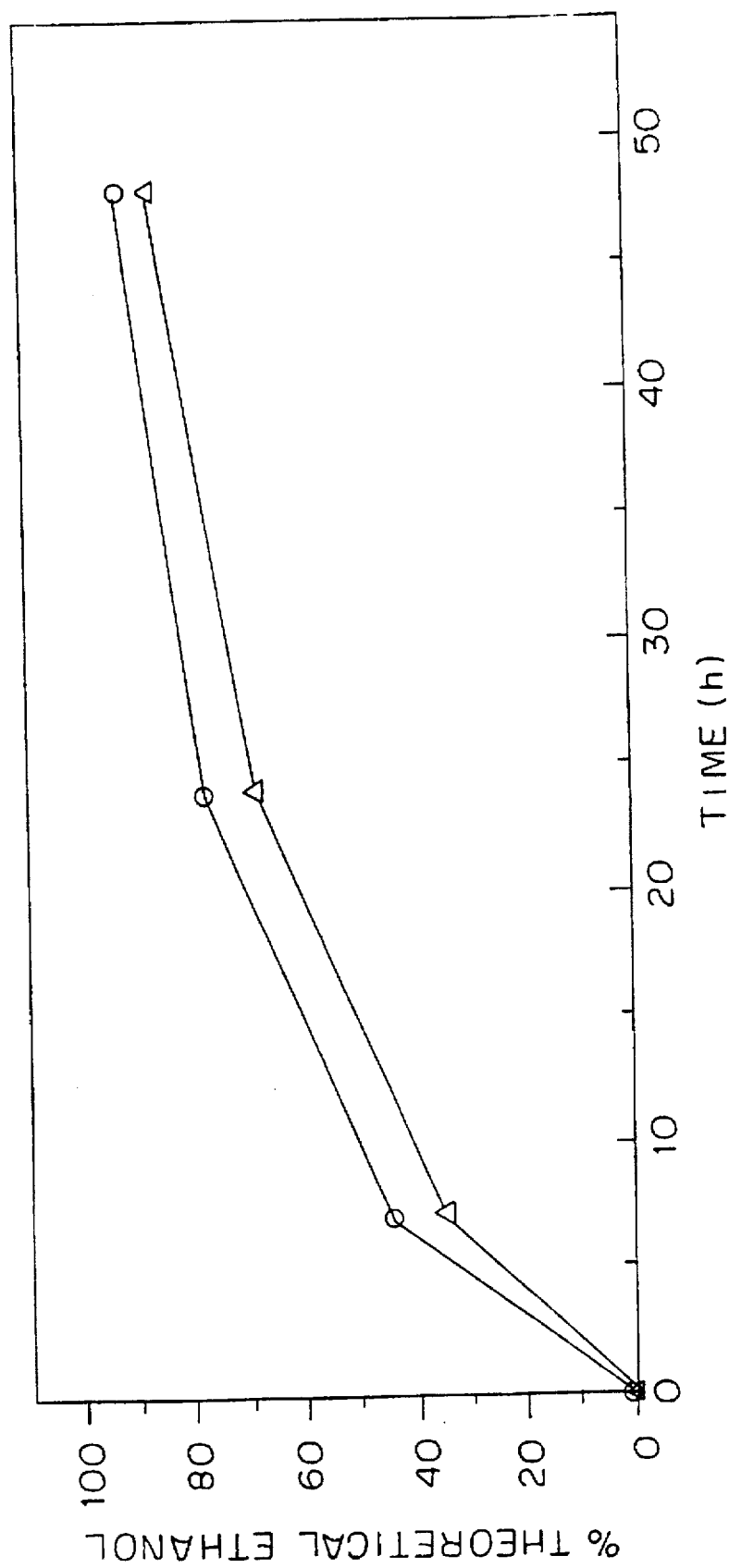
FIG. 4b displays the percentage of ethanol which can be produced theoretically from fermentation of the given amount of cellulose in a simultaneous saccharification and fermentation process. The pretreated product of the present invention is shown as circles and α-cellulose control is shown as triangles.

The percentage of cellulose digested by cellulase for the prehydrolyzed product of the present invention is represented by circles in FIG. 4a. By comparison, $\alpha$-cellulose was digested under identical conditions as a control and the data is represented by triangles in FIG. 4a. FIG. 4b displays the percentage of ethanol which is produced as compared to the theoretical maximum from fermentation of the given amount of cellulose when subjected to a simultaneous saccharification fermentation. Again, the prehydrolyzed product of the present invention is shown as circles and α-cellulose control is shown as triangles.

From the data, one can see that the cellulosic product produced in the present invention is more readily digestible and fermentable than even plain cellulose alone as represented by α-cellulose. Therefore, it appears that the prehydrolyzed solids have greater digestibility which may be due to characteristics other than simple removal of hemicellulose and lignin.

EXAMPLE 7

To a percolation reactor, which was made of Carpenter 20Cb-3 stainless steels and 2 in. (51 mm) in length by 1 in. (25 mm) in diameter, was added 3.80 g (3.53 g bone dry basis) of ambient-air-dried poplar hybrid DN 34 wood meal (−60 mesh to +80 mesh [0.18 to 0.25 mm]). Once the reactor was closed, the inlet line was attached to a water line from a high performance liquid chromatograph (HPLC) pump with the exit line being left open to the atmosphere. Water was pumped through the reactor at ambient temperature for at least 4 h to ensure total wetting of the biomass. The reactor was then submerged in a 90° C. sand bath with water being pumped through the reactor until the center of the reactor reached 88° C. The reactor was then heated for an additional 10 min to allow the trapped air in the wood pores to escape. The reactor temperature was then changed to 140° C. and a volume equal to one total void (21.4 ml) of dilute sulfuric acid solution (0.73 wt %) was pumped through the reactor and collected for 30 minutes solubilizing the "easy-to-hydrolyze" carbohydrate and concomitantly some Klason lignin. The reactor temperature was then changed to 170° C. and a volume of the acid solution equal to one total void (21.4 ml) was then pumped through the reactor and collected for 20 minutes to solubilize the "hard-to-hydrolyze" carbohydrate fraction and again concomitantly solubilize some Klason lignin. The reactor contents were then flushed with a volume of water equal to three total voids (64.2 ml) at 170° C. The collected liquor fractions which were combined, and the solid fraction were then chemically analyzed.

The chemical analysis of the pretreated solid substrate indicated that 44% of the Klason lignin in the starting biomass had been solubilized, while 94% of the starting xylan and 16% of the starting cellulose were solubilized. Similar data resulted when only one prehydrolysis condition of 170° C. for 20 minutes was used when comparing removal of hemicellulose and lignin from a lignocellulosic material.

EXAMPLE 8

To demonstrate that a flow-through reactor is more effective at separation of hemicellulose and lignin from cellulose, applicants ran a pair of experiments in exactly the same percolation apparatus. The reactor was filled with the same amount of lignocellulosic feed, dilute (0.73%) sulfuric acid was added, and the reactor was heated to 170° C. for 10 minutes. Fluid was not pumped through the reactor.

In one experiment, 170° water was pumped through the reactor at the end of the heat treatment. This was called the "hot flushed" experiment. In the other set of experiments, the reactor was cooled to ambient temperatures and its contents emptied, followed by washing the reactor contents by water at ambient temperature. This was called the "cold flushed" experiment. The solid residue was weighed wet, dried and weighed dry and the amount of each component was determined as above.

|  | Feed | Cold Flushed | Hot Flushed |
|---|---|---|---|
| "Wet" Residue (g) | 5.5 | 9.9 | 10.7 |
| % Total Solids | 92.86 | 30.98 | 26.73 |
| Dry Residue (g) | 5.11 | 3.07 | 2.86 |
| Dry Weight Percent | | | |
| Glucose | 48.56 | 65.12 | 68.54 |
| Xylose | 18.24 | 2.04 | 1.46 |
| Arabinose | 2.01 | 0.78 | 0.67 |
| Galactose | 1.10 | 0.56 | 0.44 |
| Manose | 3.45 | 1.64 | 1.41 |
| Klason Lignin | 25.22 | 34.35 | 32.00 |
| Acid Sol. Lignin | 2.74 | 1.89 | 0.85 |
| Ash | 1.35 | 0.36 | 0.48 |
| Grams | | | |
| Glucose Equivalents | 2.48 | 2.00 | 1.96 |
| Xylose Equivalents | 0.93 | 0.06 | 0.04 |
| Arabinose Equivalents | 0.10 | 0.02 | 0.02 |
| Galactose Equivalents | 0.06 | 0.02 | 0.01 |
| Manose Equivalents | 0.18 | 0.05 | 0.04 |
| Klason Lignin | 1.29 | 1.05 | 0.06 |
| Acid Sol. Lignin | 0.14 | 0.06 | 0.02 |

Note:
Glucose equivalents = glucose and glucose oligomers expressed in terms of the weight of total glucose units, etc.

Percent Removed From Feed

|  | Cold Flushed | Hot Flushed |
|---|---|---|
| Glucose | 19.47 | 20.96 |
| Xylose | 93.28 | 95.52 |
| Arabinose | 76.70 | 81.33 |
| Galactose | 69.43 | 77.60 |
| Manose | 71.45 | 77.11 |
| Klason Lignin | 18.21 | 28.94 |
| Acid Sol. Lignin | 58.58 | 82.63 |

As one can easily see, the hot flush removed more of each of the sugars derived from hemicellulose and more of the lignin. The amount of glucose removed was clearly not as significant. Most important is the percentage of Klason lignin removed. Previous attempts at acid hydrolysis have not been successful at separating appreciable amounts of lignin from the lignocellulose.

By removing greater amounts of hemicellulose and especially greater amounts of lignin, the cellulose remaining is more accessible and more readily saccharified by cellulase enzyme complex. This has been demonstrated by using the cellulase digestion process described below in Example 6. The results are as follows:

| Digestion | Percent Digested | | |
|---|---|---|---|
| Time (hrs) | Cold Flush | Hot Flush | Untreated |
| 0 | 0 | 0 | 0 |
| 4 | 25.6 | 32.7 | 4.4 |
| 8 | 42.4 | 49.4 | 5.8 |
| 24 | 78.9 | 82.9 | 9.2 |
| 72 | 97.2 | 103.0 | 11.8 |
| 144 | 98.1 | 103.8 | 12.8 |

The data appears to indicate that both the rate of cellulose digestion as well as the overall amount of cellulose digested is increased by using the hot flush technique as compared to the cold flush technique. Therefore, even a single flushing of the reactor while it is undergoing or at the end of prehydrolysis has a beneficial effect to prepare a cellulosic product which is more easily degraded by cellulase.

EXAMPLE 9

Using the percolation reactor of the previous Examples, the process was repeated with the hybrid poplar lignocellulosic substrate with only hot water being used as the degrading chemical. The prehydrolyzate liquor was continuously withdrawn and its components were measured as in the previous Examples. The solid residue was subjected to the same cellulase treatment.

A number of different combinations of temperature and time were used to represent different degrees of severity. These were 30 minutes at 120° C., 30 minutes at 140° C., 30 minutes at 160° C., 60 minutes at 160° C. and 90 minutes at 160° C. Generally speaking, the more severe the conditions, the greater glucan, xylan and klason lignin removal from the solids and the greater the digestibility.

The substrate and prehydrolyzed solids were analyzed to determine the percent of each component removed from the solids by using the hot water treatment. The results are as follows:

| Component Removal From Lignocellulosic Substrate | | | |
|---|---|---|---|
| Prehydrolysis Conditions | Xylan Removed | Klason Lignin Removed | Glucan Removed |
| 30 minutes 120° C. | 1% | 6% | 0.5% |
| 30 minutes 140° C. | 1% | 18% | 1% |
| 30 minutes 160° C. | 20% | 17% | 1% |
| 60 minutes 160° C. | 57% | 30% | 3% |
| 90 minutes 160° C. | 69% | 34% | 4% |

Figure 5:
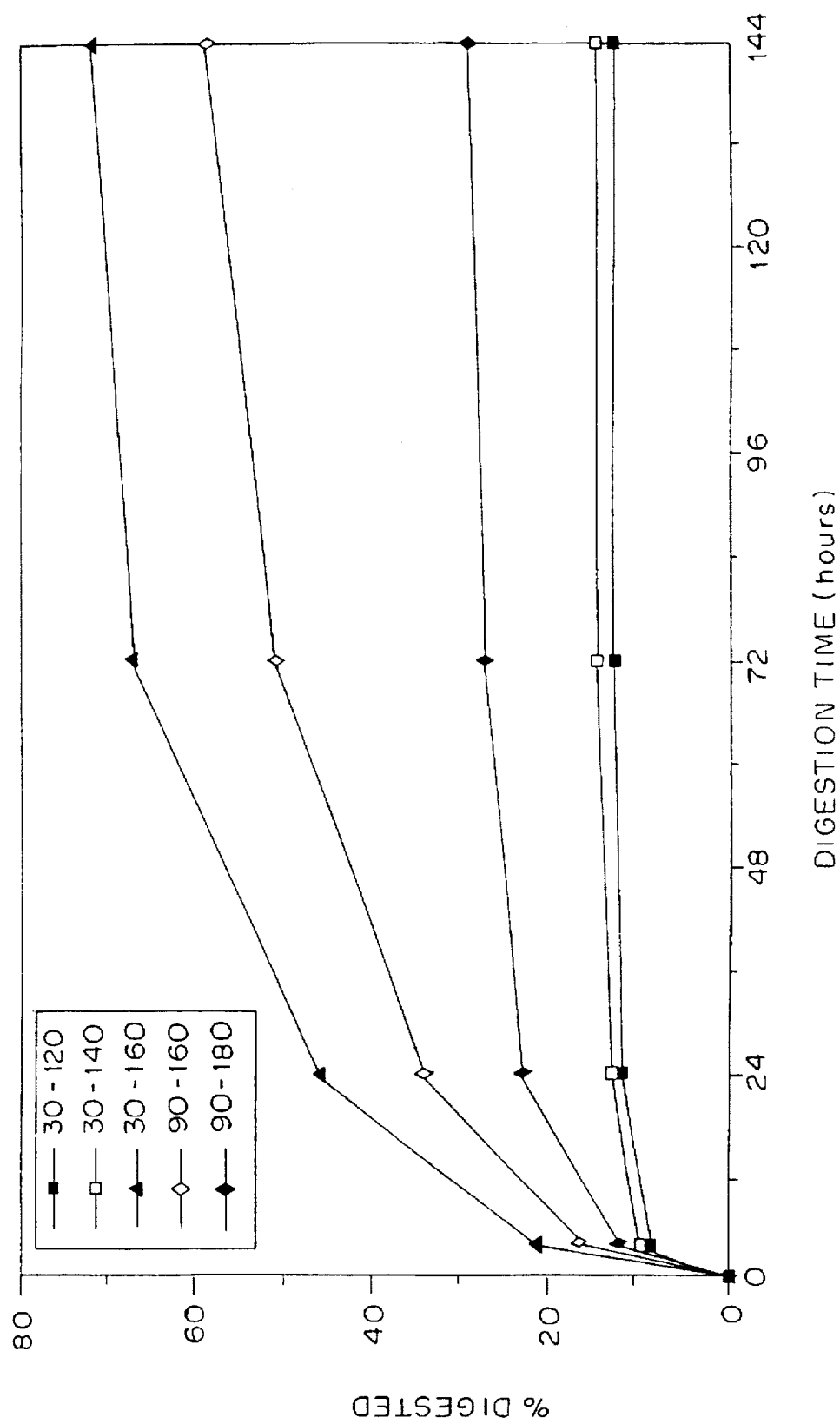
FIG. 5 displays the percentage of cellulose digested over time for hot water prehydrolysis. In the legend, the first number represents time and the second represents temperature employed during the prehydrolysis.

Levels of furfural and hydroxymethyl furfural were measured and found to be undetectable in all prehydrolysis runs. The solids were enzymatically digested with cellulase. This data is presented as FIG. 5.

While some improvement over no prehydrolysis was noted, the digestibility of hot water prehydrolyzed lignocellulosic material was considerably less than that noted in FIG. 4 generated from the acid prehydrolysis of the Example above.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

What is claimed is:

1. A process for prehydrolyzing lignocellulosic material comprising:

placing solid lignocellulosic material in a prehydrolysis reactor;

adding an acidic liquid to said solid lignocellulosic material to make a mixture;

heating the mixture to reaction temperature;

maintaining reaction temperature for time sufficient to fractionate the lignocellulosic material into a solubilized portion containing at least 20% of the lignin from the lignocellulosic material and a solid fraction containing cellulose;

removing said solubilized portion from the solid fraction while at or near reaction temperature wherein said cellulose in the solid fraction is rendered more amenable to enzymatic digestion;

and recovering said solubilized portion.

2. The process according to claim 1, wherein said reaction temperature is about 120° C. to about 240° C. and the solubilized portion has a pH of about 1 to about 5.5.

3. The process according to claim 1, wherein said acidic liquid is continuously added throughout said prehydrolysis.

4. The process according to claim 1, wherein at least one condition of the prehydrolysis is changed during the prehydrolysis.

5. The process according to claim 4, further comprising passing the acidic liquid into and through said prehydrolysis reactor before or during a change in at least one condition.

6. The process according to claim 1, wherein the prehydrolysis reactor is a flow-through reactor.

7. The process according to claim 1, wherein said solubilized portion comprises pentose, oligomers of pentose and a significant amount of lignin, said solid material contains cellulose, substantially no hemicellulose and a significantly reduced amount of lignin compared to said lignocellulosic material.

8. The process according to claim 1, further comprising removing the solid material from said prehydrolysis reactor.

9. A process for producing sugar from lignocellulosic material comprising;

placing solid lignocellulosic material in a prehydrolysis reactor;

adding an acidic liquid to said lignocellulosic material to make a mixture;

heating the mixture to reaction temperature;

maintaining reaction temperature for time sufficient to solubilize a sufficient portion of lignocellulosic material to render the cellulose therein enzymatically digestible;

removing solubilized portion from the solid material while at or near reaction temperature;

recovering said solubilized portion;

hydrolyzing sugar contained in the solubilized portion;

removing the solid material from the prehydrolysis reactor;

allowing the solid material to cool to enzymatically digestible temperature;

adding at least one enzyme capable of digesting cellulose to glucose to the solid material; and digesting cellulose in the solid material with the enzyme to produce glucose;

recovering the glucose.

10. The process according to claim 9, wherein said reaction temperature is about 120° C. to about 240° C. and the solubilized portion has a pH of about 1 to about 5.5.

11. The process according to claim 9, wherein said acidic liquid is continuously added throughout said prehydrolysis.

12. The process according to claim 9, wherein at least one condition of the prehydrolysis is changed during the prehydrolysis.

13. The process according to claim 9, further comprising passing the acidic liquid into and through said prehydrolysis reactor before or during a change in at least one condition.

14. The process according to claim 9, wherein the prehydrolysis reactor is a flow-through reactor.

* * * * *